US012629531B2

(12) United States Patent
Doerr et al.

(10) Patent No.: US 12,629,531 B2
(45) Date of Patent: May 19, 2026

(54) IMPLANTABLE DEFIBRILLATION SYSTEM

(71) Applicant: BIOTRONIK SE & Co. KG, Berlin (DE)

(72) Inventors: Thomas Doerr, Berlin (DE); Gernot Kolberg, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 457 days.

(21) Appl. No.: 17/631,744

(22) PCT Filed: Aug. 10, 2020

(86) PCT No.: PCT/EP2020/072360
§ 371 (c)(1),
(2) Date: Jan. 31, 2022

(87) PCT Pub. No.: WO2021/028377
PCT Pub. Date: Feb. 18, 2021

(65) Prior Publication Data
US 2022/0273959 A1      Sep. 1, 2022

(30) Foreign Application Priority Data

Aug. 12, 2019    (EP) ..................................... 19191170

(51) Int. Cl.
A61N 1/39        (2006.01)
A61N 1/05        (2006.01)
(52) U.S. Cl.
CPC ......... A61N 1/3956 (2013.01); A61N 1/0563 (2013.01)
(58) Field of Classification Search
CPC ........................... A61N 1/3956; A61N 1/0563
See application file for complete search history.

(56) References Cited

U.S. PATENT DOCUMENTS 5,374,279 A * 12/1994 Duffin, Jr. ............ A61N 1/3956
                                                            607/37
5,545,189 A * 8/1996 Fayram ................ A61N 1/3752
                                                            607/36

(Continued)

FOREIGN PATENT DOCUMENTS

WO        2017196477 A1    11/2017

OTHER PUBLICATIONS

International Search Report (PCT/ISA/210) and Written Opinion (PCT/ISA/237) mailed on Oct. 12, 2020, by the European Patent Office as the International Searching Authority for International Application No. PCT/EP2020/072360.

(Continued)

*Primary Examiner* — Eric D. Bertram
(74) *Attorney, Agent, or Firm* — Buchanan Ingersoll & Rooney PC

(57)        ABSTRACT

A defibrillation generator for an implantable defibrillation system comprises a housing, a connector block for connecting an electrode lead assembly to be non-transvenously implanted in a patient, and control device for controlling the operation of the defibrillation generator. The connector block has two connectors, to each of which an electrode lead of the electrode lead assembly, said electrode leads having at least one defibrillation electrode pole, is connectable, wherein the control device is configurable to assume a first operating state if an electrode lead is connected to just one of the two connectors, or a second operating state if electrode leads are connected to each of the two connectors.

12 Claims, 5 Drawing Sheets

(56)                References Cited

U.S. PATENT DOCUMENTS

| | | | | |
|---|---|---|---|---|
| 5,557,210 A * | 9/1996 | Cappa | A61N 1/0587 | |
| | | | 324/539 | |
| 5,778,881 A * | 7/1998 | Sun | A61B 5/7203 | |
| | | | 600/509 | |
| 5,899,930 A * | 5/1999 | Flynn | A61N 1/3752 | |
| | | | 607/37 | |
| 6,217,525 B1 * | 4/2001 | Medema | A61B 5/308 | |
| | | | 607/5 | |
| 7,218,960 B1 * | 5/2007 | Min | A61B 5/349 | |
| | | | 600/509 | |
| 7,398,123 B1 * | 7/2008 | Levine | A61N 1/368 | |
| | | | 607/9 | |
| 8,200,335 B2 * | 6/2012 | Donofrio | H01R 13/5224 | |
| | | | 607/37 | |
| 2004/0215240 A1 * | 10/2004 | Lovett | A61N 1/3622 | |
| | | | 607/4 | |
| 2004/0230273 A1 | 11/2004 | Cates et al. | | |
| 2007/0073346 A1 * | 3/2007 | Corbucci | A61N 1/37 | |
| | | | 607/9 | |

| | | | | |
|---|---|---|---|---|
| 2008/0208290 A1 * | 8/2008 | Phillips | A61N 1/3752 | |
| | | | 607/59 | |
| 2008/0262582 A1 * | 10/2008 | Alexander | A61N 1/3752 | |
| | | | 607/116 | |
| 2010/0106215 A1 * | 4/2010 | Stubbs | A61N 1/025 | |
| | | | 607/37 | |
| 2012/0108991 A1 * | 5/2012 | Song | A61B 5/1118 | |
| | | | 600/509 | |
| 2013/0138170 A1 * | 5/2013 | Ternes | A61B 5/7217 | |
| | | | 607/18 | |
| 2013/0165985 A1 * | 6/2013 | Ternes | A61N 1/362 | |
| | | | 607/25 | |
| 2014/0330328 A1 * | 11/2014 | Christie | A61N 1/3925 | |
| | | | 607/4 | |
| 2016/0045754 A1 | 2/2016 | Libbus et al. | | |

OTHER PUBLICATIONS

Search Report mailed on Dec. 18, 2019 by the European Patent Office for Application No. 19191170.0.

\* cited by examiner

IMPLANTABLE DEFIBRILLATION SYSTEM

CROSS-REFERENCE TO RELATED APPLICATIONS

This application is the United States National Phase under 35 U.S.C. § 371 of PCT International Patent Application No. PCT/EP2020/072360, filed on Aug. 10, 2020, which claims the benefit of European Patent Application No. 19191170.0, filed on Aug. 12, 2019, the disclosures of which are hereby incorporated by reference herein in their entireties.

TECHNICAL FIELD

The present invention relates to a defibrillation generator according to the claims, to an implantable defibrillation system, and to a method for configuring an implantable defibrillation system.

BACKGROUND

Such a defibrillation generator comprises a housing, a connector block for connection of an electrode lead assembly which is to be implanted non-transvenously in a patient, and a control device for controlling the operation of the defibrillation generator.

Such a defibrillation system, also known as an implantable cardioverter-defibrillator (ICD for short), is used to detect and treat potentially life-threatening cardiac arrhythmias (ventricular tachycardia, bradycardia, ventricular fibrillation). Such a defibrillation system is implanted in a patient in such a way that one or more electrode leads, starting from a defibrillation generator, extend to the human heart in order, on the one hand, to pick up signals there for the purpose of detecting cardiac arrhythmias and, on the other hand, to emit stimulation energy, in particular to cause an electric shock (defibrillation). In this case both the electrode leads and the defibrillation generator are permanently implanted and remain in the patient for a relatively long period of time, usually several years.

In conventional defibrillation systems, the defibrillation generator is implanted subcutaneously and electrode leads are laid transvenously directly into the heart via a vein access. Although such defibrillation systems have proven their worth in practice, it may be desirable to provide other defibrillation systems that are easier to implant, can be retrofitted as appropriate by adding further electrode leads, and are also easier to remove, in particular avoiding direct transvenous access into the heart.

The present disclosure is directed toward overcoming one or more of the above-mentioned problems, though not necessarily limited to embodiments that do.

SUMMARY

An object of the present invention is to provide a defibrillation generator, an implantable defibrillation system, and a method for configuring an implantable defibrillation system that enable simple implantation with variable applicability and, as appropriate, the option for retrofitting with additional electrode leads.

At least this object is achieved by a subject having the features of claim 1.

Accordingly, the connector block has two connectors, to each of which an electrode lead of the electrode lead assembly, said electrode leads each having at least one defibrillation electrode pole, is connectable, the control device being configurable to assume a first operating state if an electrode lead is connected just to one of the two connectors, or a second operating state if electrode leads are connected to each of the two connectors, so as to provide a defibrillation function in the first operating state via the one electrode lead connected to one of the connectors, and so as to provide a defibrillation function in the second operating state via the electrode leads connected to the two connectors.

The defibrillation generator has a connector block which has two (or more) connectors. The defibrillation generator may be equipped here selectively with one or with more electrode leads of an electrode lead assembly to be implanted non-transvenously in a patient, so that the defibrillation generator may be operated with merely one connected electrode lead or with two connected electrode leads or possibly also with more than two connected electrode leads.

The electrode leads of the electrode lead assembly are to be implanted non-transvenously in a patient. This is to be understood to mean that the electrode leads of the electrode lead assembly are to be laid outside the patient's heart, for example subcutaneously or submuscularly. The electrode leads of the electrode lead assembly to be implanted non-transvenously thus do not extend via a venous access into the patient's heart, but instead run outside the heart.

It is not ruled out that, in addition to the electrode leads of the electrode lead assembly to be implanted non-transvenously, further electrode leads are present and might be intended for implantation in the heart transvenously. Such additional electrode leads, as will be explained later, may be used, for example, for intracardiac sensing and/or stimulation.

The defibrillation generator is intended to be able to be operated with just one connected electrode lead of the electrode lead assembly or with more than one connected electrode lead. The defibrillation generator in this case is designed to provide a defibrillation function, and therefore electrical stimulation energy, for example with a maximum energy of 45 J or above, can be delivered via a connected electrode lead assembly, in order to effect a defibrillation in the event that a cardiac arrhythmia is detected.

The control device of the defibrillation generator is configurable so as to assume a first operating state or a second operating state. The first operating state is designed here to provide a defibrillation function if only one electrode lead is connected to one of the two connectors of the connector block of the defibrillation generator. The second operating state, by contrast, is designed to provide a defibrillation function if electrode leads are connected to (at least) two connectors of the connector block.

Depending on whether the defibrillation generator is equipped with one electrode lead or with two electrode leads, a defibrillation function is thus provided via the one connected electrode lead or with use of two connected electrode leads. In order to switch between the different operating states, the control device may have a switching unit, for example, which is realized, for example, by an electronic assembly or is implemented by control software of the control device. In the first operating state, signals are fed merely to one connector by means of the switching unit, and, as appropriate, are received by the one connector. By contrast, in the second operating state, signals are conducted to both connectors, and, as appropriate, are received by both connectors for the purpose of the evaluation.

Since the electrode leads of the electrode lead assembly are implanted non-transvenously, a simple implantation technique results, for example with use of a tunnelling rod.

An implantation process may thus be significantly facilitated, possibly avoiding the general anaesthetic necessary for implantation and with a reduction in the operative risk. The simple implantation also allows simple retrofitting by connection of further electrode leads to a defibrillation generator already implanted; to this end, the defibrillation generator may be reconfigured in order to operate the defibrillation generator with further electrode leads.

In one embodiment, the connector block has a third connector for connection of an electrode lead that is to be transvenously implanted intracardially. By means of such an electrode lead that is to be transvenously implanted intracardially, intracardiac stimulation and/or sensing of intracardiac signals, for example atrial signals and/or ventricular signals, may be implemented, for example. Such an additional third electrode lead, in contrast to the electrode leads of the electrode lead assembly to be implanted non-transvenously, is to be laid transvenously into the heart, so that the defibrillation generator may also be operated additionally with a transvenous electrode lead.

Additionally or alternatively, the connector block may have a fourth connector for connection of a coronary sinus electrode lead that is to be implanted transvenously. Such a coronary sinus electrode lead may be laid into the heart for the left-ventricular stimulation and/or sensing.

In any case, the control device may be configurable in order to operate the defibrillation generator with or without an additional, transvenous electrode lead connected to the third connector and/or the fourth connector.

If two electrode leads of the electrode lead assembly, which each have a defibrillation electrode pole for delivering stimulation pulses for the purpose of defibrillation, are connected to the defibrillation generator, defibrillation may be performed with use of the defibrillation electrode poles of the electrode leads, said defibrillation electrode poles forming a dipole. If just one electrode lead is connected to one of the two connectors of the connector block, the electrode lead may possibly have two defibrillation electrode poles, which form a dipole for delivering stimulation energy for the purpose of defibrillation.

Both with two electrode leads, each having a defibrillation electrode pole, connected to the defibrillation generator, and with a single electrode lead, having one or more defibrillation electrode poles, connected to the defibrillation generator, however, the housing of the defibrillation generator may also serve as a counter-electrode, so that a dipole is formed between a defibrillation electrode pole of one electrode lead and the housing of the defibrillation generator.

In this case, the defibrillation generator may be configured to deliver defibrillation energy via a predetermined dipole (between defibrillation electrode poles of the electrode leads or between one defibrillation electrode pole and the housing of the defibrillation generator), wherein the configuration may be performed once at the time of commissioning or repeatedly during operation, for example depending on an effective excitation.

An implantable defibrillation system comprises a defibrillation generator of the above-described kind and an electrode lead assembly which is to be implanted non-transvenously in a patient. The electrode lead assembly in this case comprises, in particular, a first electrode lead for connection to a first connector of the connector block of the defibrillation generator and a second electrode lead for connection to a second connector of the connector block of the defibrillation generator. Both the first electrode lead and the second electrode lead have at least one defibrillation electrode pole, so that the electrode leads may be used jointly or separately from one another in order to deliver stimulation energy for the purpose of defibrillation.

In this case, the electrode leads may be connected optionally to the defibrillation generator, wherein the defibrillation generator may be configured differently depending on which electrode leads are connected to the defibrillation generator. Within the scope of the configuration, it may also be defined via which dipole (between different defibrillation electrode poles or between one defibrillation electrode pole and the housing of the defibrillation generator) stimulation energy is to be delivered, as appropriate, during operation for the purpose of defibrillation.

In one embodiment, the first electrode lead and/or the second electrode lead have at least one sensing electrode pole for detecting ventricular and/or atrial signals. A sensing function may thus also be provided via electrode leads of the electrode lead assembly to be implanted non-transvenously, in order to detect cardiac arrhythmias and in order to control a stimulation.

Such sensing electrode poles may be designed, for example, as ring electrodes, and thus extend annularly around the associated electrode lead.

A defibrillation electrode pole of an electrode lead, by contrast, may be designed as a helix and thus extends helically around the associated electrode lead. Due to the helical design, the surface area of the defibrillation electrode pole is enlarged, so that electric shock energy may be delivered and introduced into the heart in an efficient manner, while still providing sufficient flexibility on the electrode lead for flexible, possibly curved arrangement in the patient.

In one embodiment, an atrial sensing electrode pole of an electrode lead of the electrode lead assembly is arranged at a distal end of the electrode lead in question. In this case, the distal end corresponds to the end of the electrode lead that is remote from a proximal end connectable to the defibrillation generator. In this embodiment, the atrial sensing electrode pole is thus placed distally from the defibrillation generator, wherein the atrial sensing electrode pole may be arranged directly at the distal end and in this case, for example, covers the tip of the electrode lead. In the implanted state, the electrode lead with the atrial sensing electrode pole arranged thereon approaches, for example, the right atrium of the heart of the patient, so that atrial signals may be recorded via the atrial sensing electrode pole and may be fed to the defibrillation generator.

A sensing electrode pole used to record atrial signals may, however, additionally or alternatively, also be arranged in a manner approximately offset from the distal end of the electrode lead, wherein, however, the sensing electrode pole is arranged distally from the proximal end of the electrode lead.

In one embodiment, at least one of the electrode leads of the electrode lead assembly has two sensing electrode poles, which form a dipole for detecting atrial signals. The two sensing electrode poles may be arranged, for example, in the region of the distal end of the electrode lead. However, it is also possible that the sensing electrode poles are arranged at a greater distance from one another on the electrode lead. Signals originating from atrial activity of the heart may be recorded between the two sensing electrode poles and thus make it possible to detect atrial sensing signals.

In one embodiment, an atrial sensing electrode pole is arranged on a first side of a defibrillation electrode pole, and a ventricular sensing electrode pole is arranged on a second side of the defibrillation electrode pole of an electrode lead. Atrial signals and ventricular signals are thus sensed, more-over via different sensing electrode poles at different locations of the electrode lead axially offset from one another.

In one embodiment, the defibrillation system has a third electrode lead for connection to a third connector of the connector block of the defibrillation generator. Such a third electrode lead may be intended for implantation transvenously in the heart and has an electrode array having one or more electrode poles, for example in order to record signals intracardially in the right ventricle or in the right atrium, or in order to bring about a stimulation. The control device of the defibrillation generator may be configurable in this case in such a way that signals may be received via the electrode lead for the purpose of the sensing and/or signals may be delivered to the third electrode lead for the purpose of the stimulation.

In one embodiment, each electrode lead of the electrode lead assembly has a plug, which may be inserted into an associated socket connector of the defibrillation generator in order to connect the electrode lead to the defibrillation generator. In this case, for example, all electrode poles of the electrode lead may be connected functionally to the defibrillation generator via a single plug. For example, the plug may have connection connectors which, in the event that the plug is plugged to the socket connector of the defibrillation generator, electrically contact associated contact elements of the socket connector, so that electrical supply lines of the electrode lead connected to the defibrillation generator.

For example, the plug may have two poles, four poles, six poles, eight poles, or also more poles.

In one embodiment, the control device of the defibrillation generator may have a first receiving channel for processing ventricular signals received via the electrode lead assembly and a second receiving channel for processing atrial signals received via the electrode lead assembly. Separate receiving channels are thus provided for the recording and processing of atrial signals, in which channels the atrial signals may be processed separately. In particular, the second receiving channel for processing the atrial signals may have a different gain and a different filter characteristic as compared to the first receiving channel for processing the ventricular signals. In this way, atrial signals may be received with greater sensitivity, for example with a sensitivity less than 1 mV, preferably less than 0.1 mV, more preferably less than 0.05 mV.

In this case, atrial signals may be filtered particularly, in particular in order to suppress other, possibly interfering signals, for example ventricular signals, for example with use of a cyclic time window, in which interfering signals may be suppressed (what is known as a "blanking window"). In this case, atrial signals may additionally be processed, in order to analyse signal characteristics, for example a maximum (positive and/or negative) amplitude, a peak-to-peak value, a pulse width, or a (positive and/or negative) average value.

An object is also achieved by a method for configuring an implantable defibrillation system, comprising the steps of: providing a defibrillation generator, which has a housing, a connector block for connection of an electrode lead assembly, and a control device for controlling the operation of the defibrillation generator; providing an electrode lead assembly comprising at least one electrode lead, wherein the electrode lead assembly is to be implanted non-transvenously in a patient; either connecting one electrode lead of the electrode lead assembly, said electrode lead having at least one defibrillation electrode pole, to one of two connectors of the connector block, or connecting two electrode leads of the electrode lead assembly, each electrode lead having at least one defibrillation electrode pole, to the two connectors of the connector block; and configuring a switching unit of the control device to assume a first operating state if only one electrode lead is connected to one of the two connectors, or a second operating state if electrode leads are connected to both connectors, wherein the control device in the first operating states provides a defibrillation function via the electrode lead connected to the one of the connectors and in the second operating state provides a defibrillation function via the electrode leads connected to the two connectors.

With regard to the method, the same advantages and advantageous embodiments as described above for the defibrillation generator and the defibrillation system apply, and therefore reference should be made in this regard to the full scope of the foregoing description.

The control device may be configured prior to the implantation of the defibrillation generator and the electrode lead assembly, during the implantation of the defibrillation generator and the electrode lead assembly, or after the implantation of the defibrillation generator and the electrode lead assembly.

In this case, the defibrillation generator may be implanted subcutaneously or submuscularly in a patient.

One or more electrode leads of the electrode lead assemblies may be implanted subcutaneously or submuscularly with use, for example, of a tunnelling technique. Within the scope of such a tunnelling technique, a blunt tunnelling rod, over which an "introducer" is slid, is moved through tissue of the patient, in order to define an implantation path for the arrangement of an electrode lead. The tunnelling rod is then retracted, whilst the introducer remains in its assumed position and thus forms a tunnel, through which the electrode lead may be introduced for the purpose of implantation.

The electrode lead may have a distal fixing mechanism, which may be activated when the electrode lead has reached its intended position.

Once the electrode lead has been introduced, the introducer over the electrode may be retracted in order to remove the introducer. This may be achieved by splaying the introducer (known as "peeling").

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Various concepts forming the basis of the present invention will be explained in greater detail hereinafter with reference to the embodiments shown in the drawings, in which.

DETAILED DESCRIPTION

In an embodiment shown in FIG. 1, an implantable defibrillation system has a defibrillation generator 1, which is to be implanted, for example, subcutaneously or under the chest muscle of a patient and to which an electrode lead 2 (or a plurality of electrode leads, as will be described hereinafter) of an electrode lead assembly 4 is connected. The electrode lead 2 extends here in the implanted state from the defibrillation generator 1 outside the patient's heart H and is thus implanted non-transvenously, without direct access into the heart.

Figure 1:
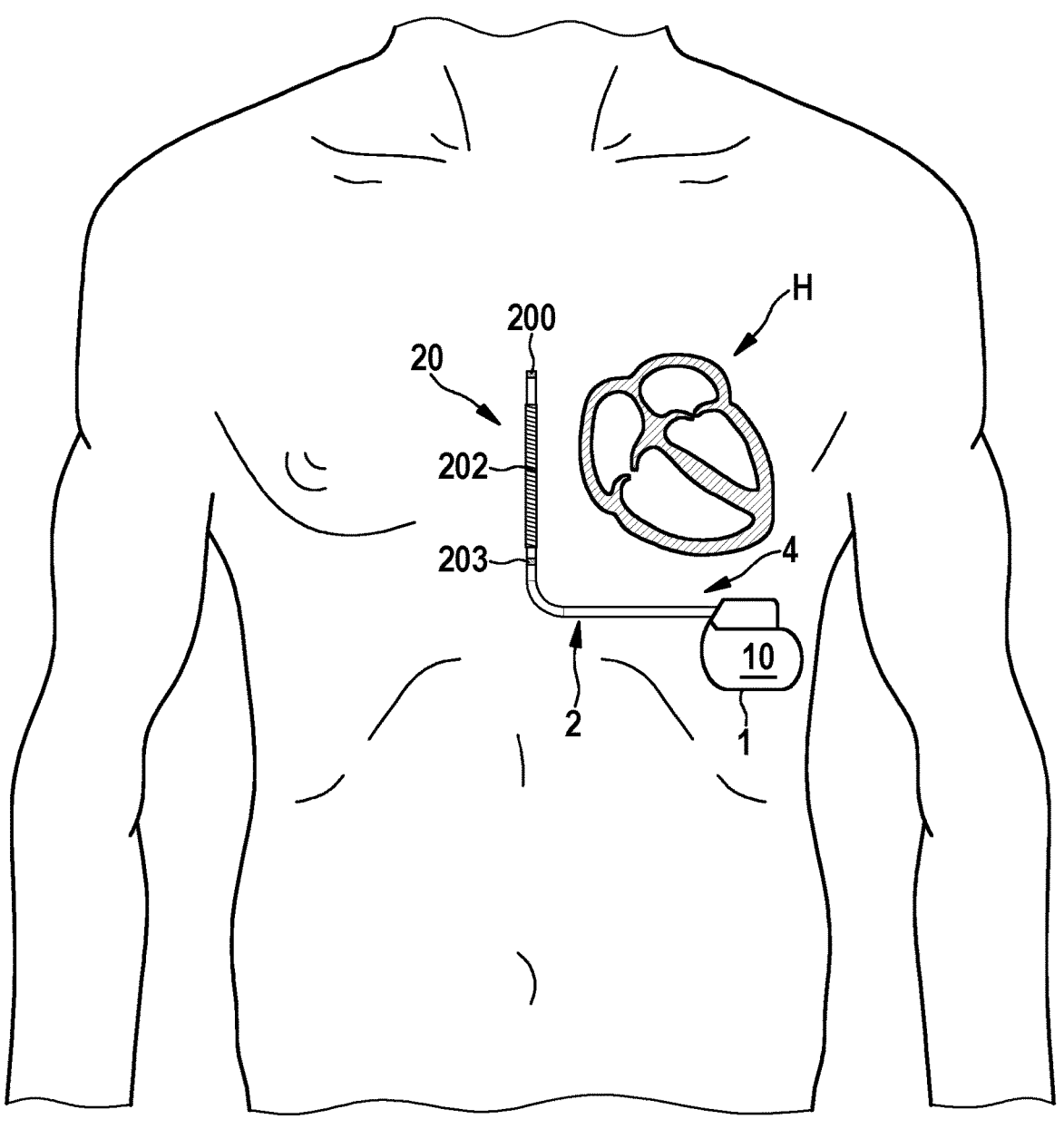
FIG. 1 shows a view of a defibrillation system with an electrode lead implanted non-transvenously and connected to a defibrillation generator.

As can be seen in FIG. 1, the electrode lead 2 thus runs outside the patient's heart H. An electrode array 20 arranged in the distal region on the electrode lead 2 approaches the heart H from the outside, so that signals from the heart H can be recorded via the electrode array 20 and, in addition, electrical signals can be delivered to the heart H for the purpose of stimulation.

In the example according to FIG. 1, the electrode array 20 of the electrode lead 2 in the implanted state is particularly close to the right atrium RA and the right ventricle RV of heart H. Via the electrode array 20, for example, both atrial signals from the right atrium RA and ventricular signals from the right ventricle RV can be recorded and, in addition, stimulation energy can be delivered for the purpose of stimulation, especially for the treatment of cardiac arrhythmias.

In the embodiment shown in FIG. 1, a (single) non-transvenous electrode lead 2 is connected to the defibrillation generator 1. In contrast, in the embodiments shown in FIGS. 2 and 3, two electrode leads 2A, 2B of a non-transvenous electrode lead assembly 4 are connected to the defibrillation generator 1, and the electrode leads 2A, 2B are each arranged non-transvenously and thus outside the patient's heart H. Each electrode lead 2A, 2B has an electrode assembly 20 with electrode poles 202, 203.

Figure 2:
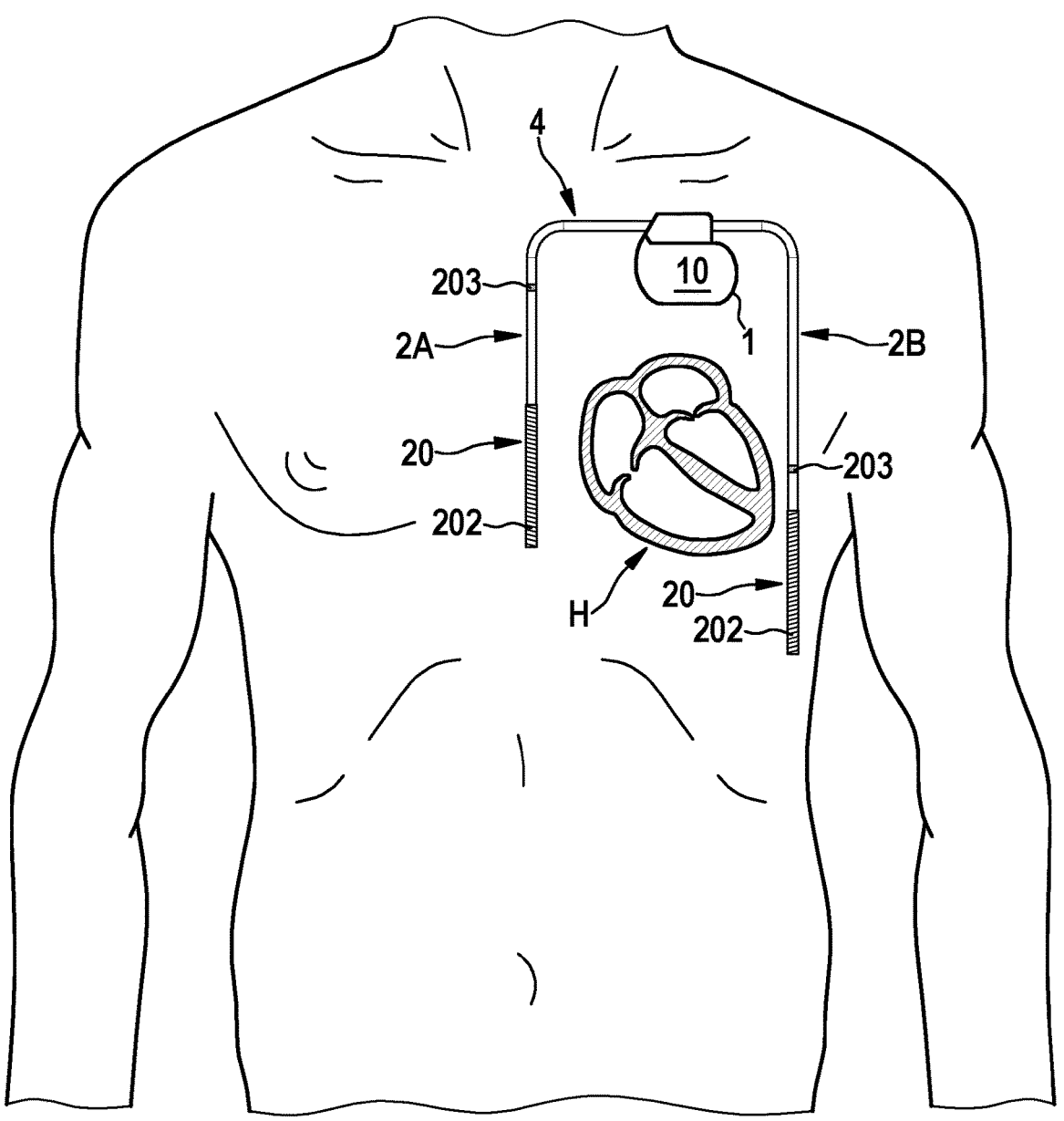
FIG. 2 shows a view of the defibrillation system with two non-transvenously implanted electrode leads connected to a defibrillation generator.
Figure 3:
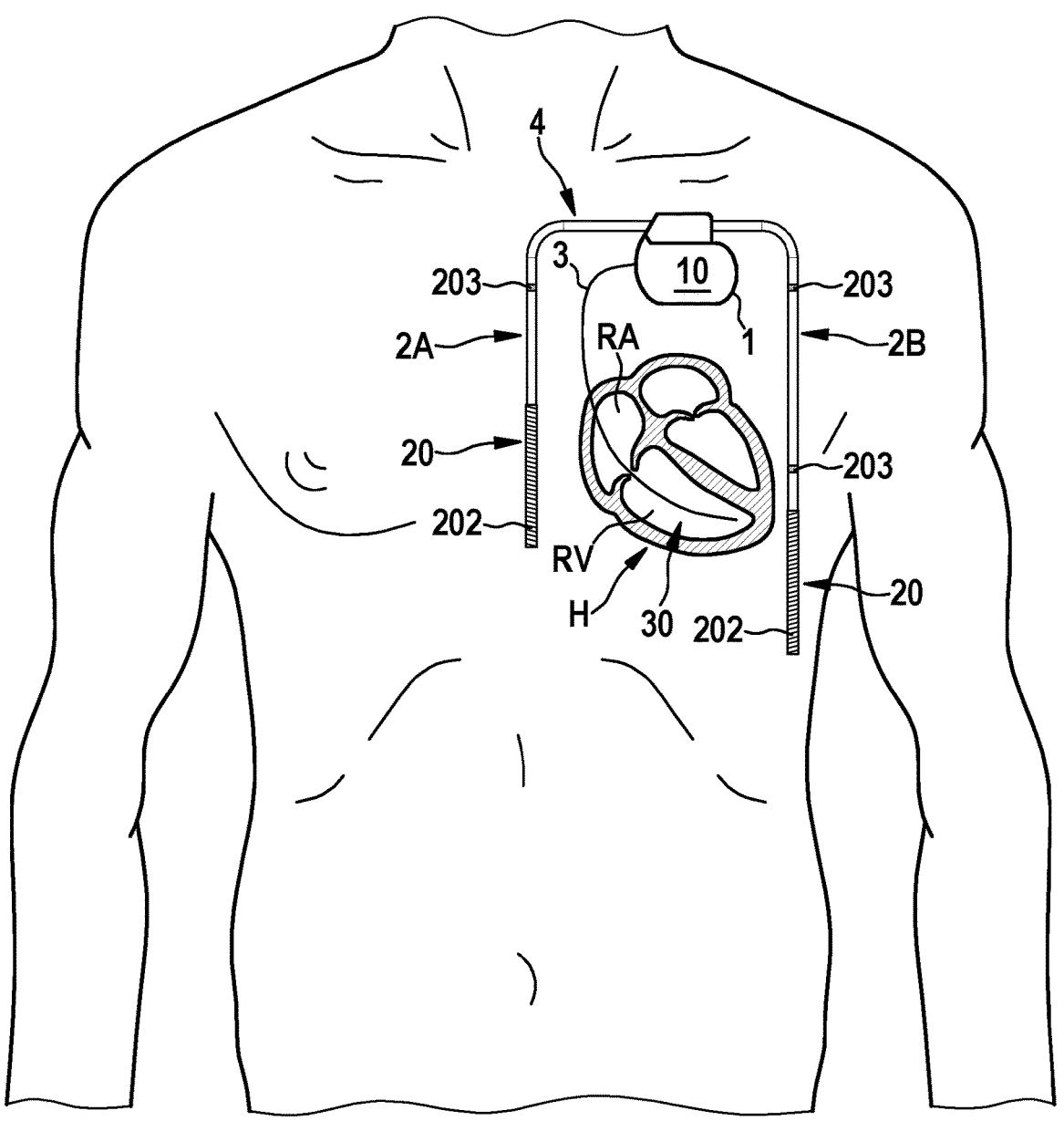
FIG. 3 shows a view of a defibrillation system with two non-transvenously implanted electrode leads connected to a defibrillation generator and an additional, transvenously implanted electrode lead.

In the embodiment shown in FIG. 3, in comparison to the embodiment according to FIG. 2, a further electrode lead 3 is additionally connected to the defibrillation generator 1, which further electrode lead is implanted transvenously and extends into the heart H, in particular—in the embodiment shown—into the right ventricle RV.

Figure 4:
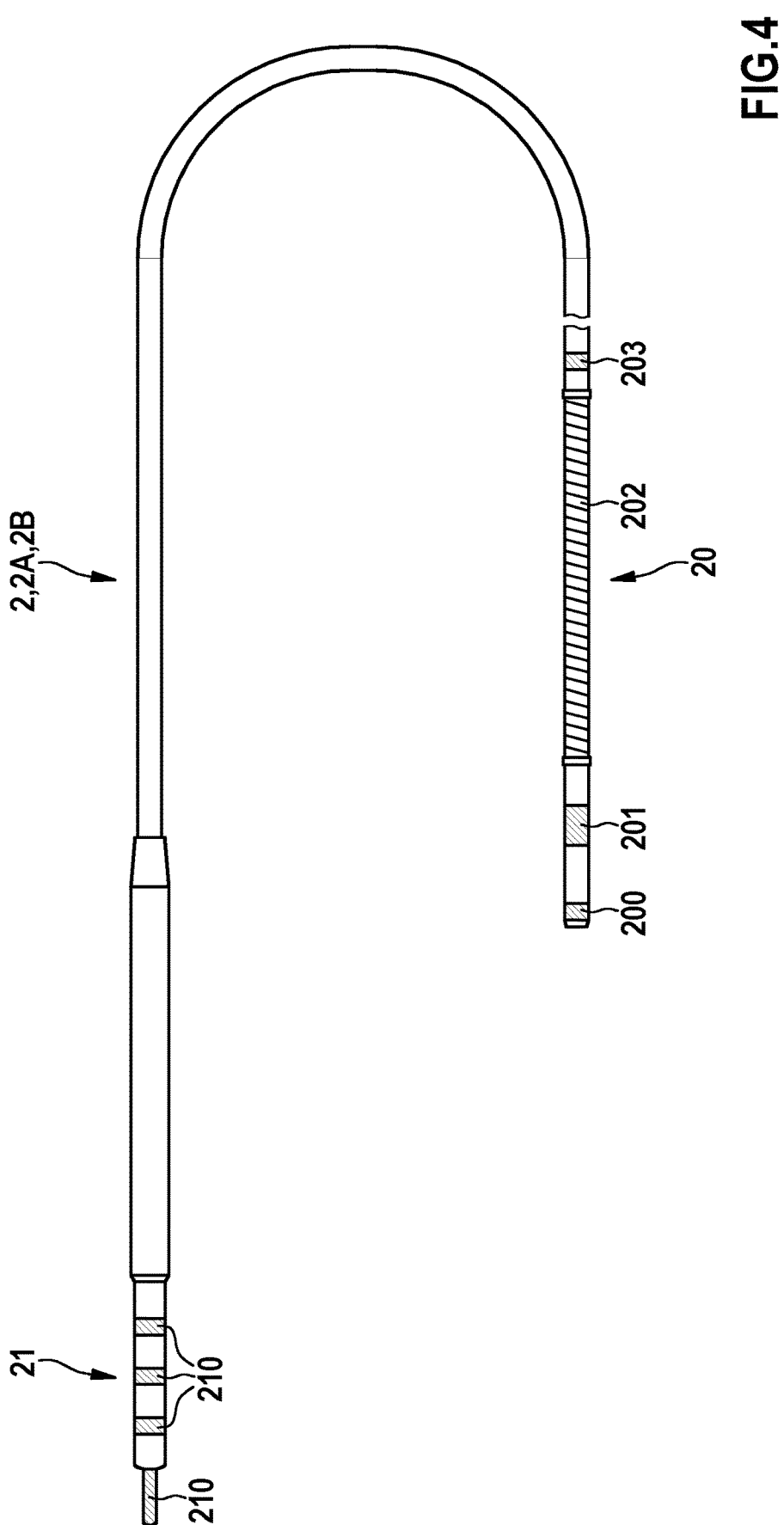
FIG. 4 shows a view of an embodiment of an electrode lead.

FIG. 4 shows an embodiment of an electrode lead 2, 2A, 2B, as can be connected to a defibrillation generator 1 either alone (FIG. 1) or together with one or more further electrode leads (FIGS. 2 and 3) in the embodiments according to FIGS. 1 to 3. In the embodiment shown, the electrode lead 2, 2A, 2B has an electrode array 20 which is formed by a plurality of electrode poles 200-203 and is arranged in the region of a distal end of the electrode lead 2. At a proximal end, the electrode lead 2, 2A, 2B has a plug 21 on which connection connectors 210 are arranged and which can be plugged into the defibrillation generator 1 in order to thus connect the electrode poles 200-203 to the defibrillation generator 1, to feed received signals to the defibrillation generator 1 and to feed stimulation energy to the electrode array 20.

The electrode array 20 has a plurality of electrode poles 200-203. Each electrode pole 200-203 can be assigned a connection terminal 210, and in this case each electrode pole 200-203 is connected to the assigned connection terminal 210 via a supply line. In this case, the number of connection connectors 210 corresponds to the number of electrode poles

200-203. Alternatively, individual electrode poles 200-203 can also be connected together to an assigned connection terminal 210.

In the embodiment shown, the plug 21 has four connection connectors 210 and is therefore four-pole. Alternatively, the plug 21 can also have a higher number of connection connectors 210, for example, and can be designed with six or eight poles, for example.

The electrode poles 200-203 are of different designs and fulfil different functions.

A first electrode pole 202, referred to as a defibrillation electrode pole, is used to deliver stimulation energy and is arranged helically on the electrode lead 2, 2A, 2B. In the embodiment shown, the electrode lead 2, 2A, 2B has a defibrillation electrode pole 202, to which stimulation energy can be supplied from the defibrillation generator 1 in order to deliver stimulation energy to the heart H for the purpose of defibrillation and to treat cardiac arrhythmias detected in this way.

A second electrode pole 203, referred to as a ventricular sensing electrode pole, is used, for example, to detect ventricular signals, i.e. signals that have a ventricular origin and are due to ventricular activity at the heart H. Such ventricular signals can be intrinsic, i.e. they can be due to an intrinsic activity of the heart. Such ventricular signals can also be stimulated.

Third electrode poles 200, 201, referred to as atrial sensing electrode poles, are arranged in the region of the distal end of the electrode lead 2 in the embodiment shown in FIG. 4. The sensing electrode poles 200, 201 are used, for example, to detect atrial signals and, with implanted electrode lead 2, 2A, 2B, are located in the immediate vicinity of the right atrium RA of the heart H, for example.

Whereas the defibrillation electrode pole 202 is formed by a helix, the ventricular sensing electrode pole 203 and the atrial sensing electrode poles 200, 201 are formed as ring electrodes, for example, which extend annularly around the electrode lead 2.

In each case, the electrode poles 200-203 can be exposed outwardly and thus make electrical contact with surrounding tissue of the patient.

The atrial sensing electrode poles 200, 201 together form a dipole in the embodiment shown, via which atrial signals can be received.

The defibrillation generator 1 is designed, as shown by way of example in FIGS. 1-3, so that one or more electrode leads 2, 2A, 2B can be connected to the defibrillation generator 1. The electrode leads 2, 2A, 2B can be designed here identically and, for example, as shown in FIG. 4. However, it is also possible that differently designed electrode leads 2, 2A, 2B, for example electrode leads 2, 2A, 2B with different numbers and arrangement of electrode poles, can be connected to the defibrillation generator 1.

Figure 5:
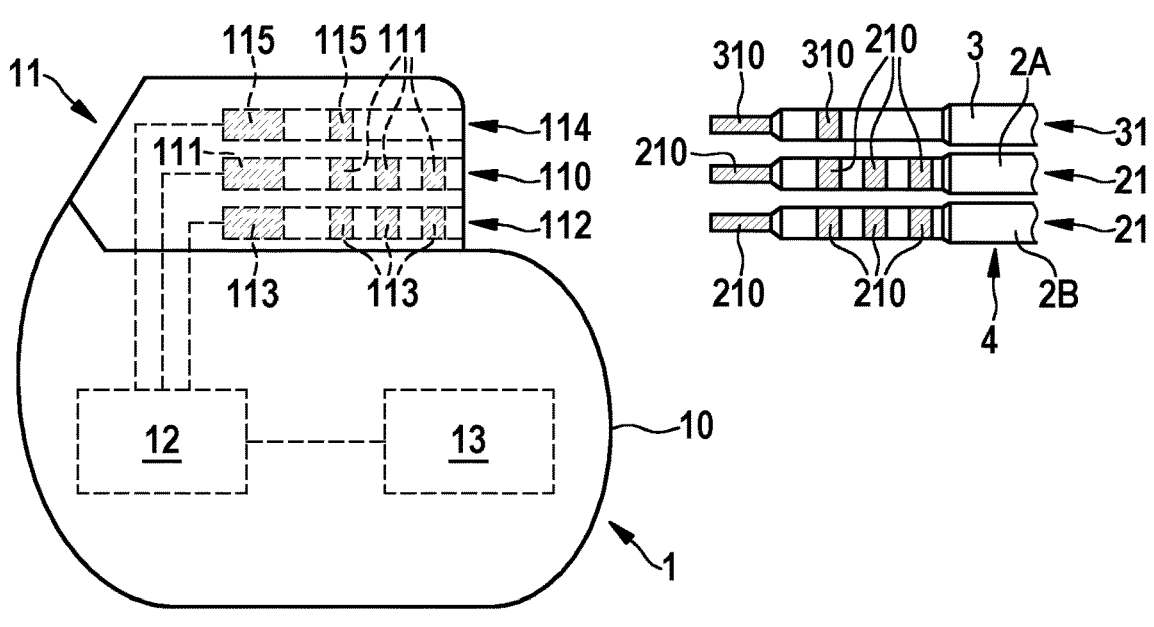
FIG. 5 shows a view of a defibrillation generator of the defibrillation system.

As shown in an embodiment in FIG. 5, the defibrillation generator 1 has a housing 10 and a connector block 11 formed on the housing 10. The connector block 11 has connectors 110, 112, 114 to which electrode leads 2, 2A, 2B, 3 can be connected, as shown by way of example in FIG. 5. Each connector 110, 112, 114 in this case forms a plug connector into which an assigned plug 21, 31 of an assigned electrode lead 2, 2A, 2B, 3 can be inserted in such a way that connection connectors 210, 310 of the plugs 21, 31 make electrical contact with assigned contact elements 111, 113, 115 of the connectors 110, 112, 114 and thus establish an electrical connection between the electrode leads 2, 2A, 2B, 3 and the defibrillation generator 1.

The defibrillation generator 1 has a control device 12 which is functionally connected to the connectors 110, 112, 114, in particular the contact elements 111, 113, 115 of the connectors 110, 112, 114, so that signals can be received from the connectors 110, 112, 114 and signals can be fed to the connectors 110, 112, 114.

The defibrillation generator 1 additionally has an energy store 13, especially in the form of a battery. The defibrillation generator 1 can be implanted in a patient and should remain in the patient for a long period of time, for example several years. All components of the defibrillation generator 1 are encapsulated by the housing 10 and are therefore enclosed in a moisture-proof manner.

The control device 12 is configurable to assume different operating states. Depending on the number and combination of electrode leads 2, 2A, 2B, 3 connected to the defibrillation generator 1, the control device 12 can be operated in different operating states in order to provide a defibrillation function for the treatment of cardiac arrhythmias.

Figure 6:
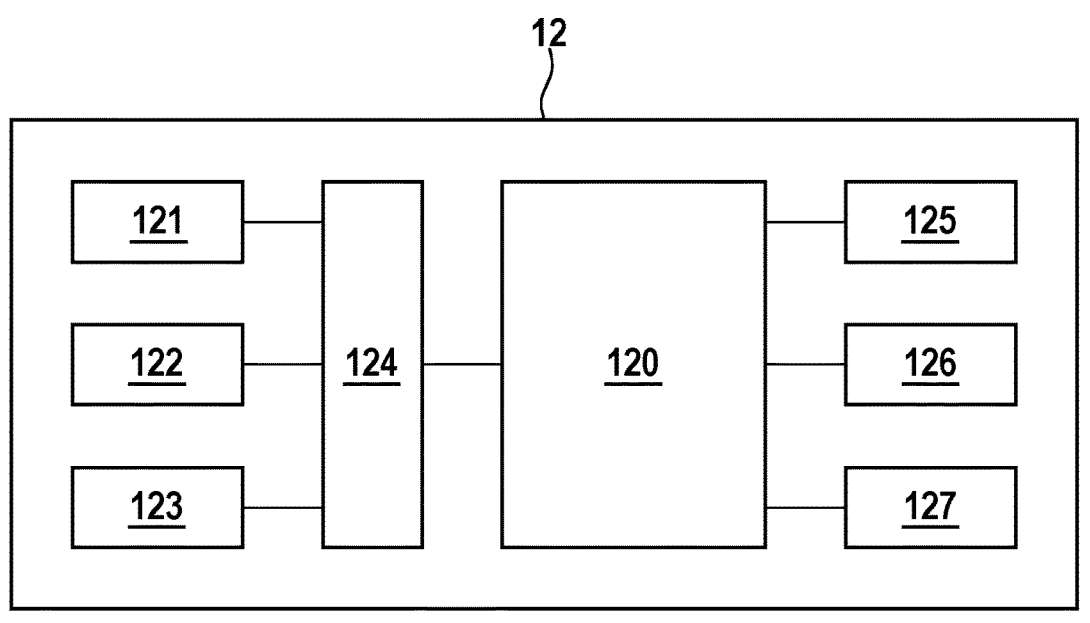
FIG. 6 shows a functional, schematic view of a control device of the defibrillation generator.

As shown schematically in FIG. 6, the control device 12 has, for example, a first connector unit 121 associated with a first connector 110, a second connector unit 122 associated with a second connector 112, and a third connector unit 123 associated with a third connector 114. The connector units 121-123 are each connected to a switching unit 124, via which the connector units 121-123 can be controlled in a variably configurable manner.

If, for example, as shown in FIG. 1, only one electrode lead 2 is connected to the connector 110, the control device 12 can be configured to receive and deliver signals only via the connector unit 121, so that a defibrillation function is provided via the electrode lead 2 connected to the connector 110.

If, on the other hand, two electrode leads 2A, 2B are connected to the connectors 110, 112 as shown in FIG. 2, signals are received and delivered via the connector units 121, 122, so that a defibrillation function can be provided using the electrode leads 2A, 2B.

If a transvenously implanted electrode lead 3 is additionally connected to the connector 114, additional signals are also received via the connector unit 123 and, if necessary, are also delivered for intracardiac stimulation.

The switching unit 124 can be realized by an electronic assembly. It is also conceivable that the switching unit 124 is implemented by means of control software and thus in software terms (without a hardware switch).

The switching unit 124 is functionally connected to a control unit 120 of the control device 12, which evaluates received signals for the purpose of diagnostics and therapy management. The control unit 120 is connected to a ventricular stimulation unit 125, an atrial stimulation unit 126 and a cardioversion/defibrillation unit 127, via which signals for ventricular and/or atrial stimulation and for defibrillation can be generated and fed to connected electrode leads 2, 2A, 2B, 3.

The control device 12 can be configured before implantation, during implantation or even after implantation. The configuration is carried out by programming, and the configuration adapts the control device 12 to a connected combination of electrode leads 2, 2A, 2B, 3 in order to be able to provide a defibrillation function via a connected combination of electrode leads 2, 2A, 2B, 3.

If necessary, the control device 12 can also be designed to automatically detect which type and combination of electrode leads 2, 2A, 2B, 3 are connected to the defibrillation generator 1 in order to automatically carry out a configuration.

Defibrillation energy (defibrillation shocks) is delivered via defibrillation electrode poles 202 of connected, non-transvenously implanted electrode leads 2, 2A, 2B.

In the embodiment shown in FIG. 1, the connected electrode lead 2 has a single defibrillation electrode pole 202, which forms a dipole together with the housing 10 of the defibrillation generator 1. The housing 10 thus represents a counter-electrode for the defibrillation electrode pole 202 of the electrode lead 2, so that, between the defibrillation electrode pole 202 and the housing 10, stimulation energy can be injected into the heart H.

In the embodiments shown in FIGS. 2 and 3, the non-transvenously implanted electrode leads 2A, 2B connected to the defibrillation generator 1 each have one defibrillation electrode pole. Stimulation energy can be delivered between the two defibrillation electrode poles 202 of the electrode leads 2A, 2B. Alternatively, the housing 10 of the defibrillation generator 1 can also be included as a counter-electrode, for example by delivering stimulation energy between the defibrillation electrode pole 202 of one of the electrode leads 2A, 2B and the combination of the defibrillation electrode pole 202 of the other electrode lead 2B, 2A and the housing 10 of the defibrillation generator 1 (the defibrillation electrode pole 202 of the other electrode lead 2B, 2A and the housing 10 of the defibrillation generator 1 serve together as counter-electrode).

In the example shown in FIG. 1, atrial and/or ventricular signals can be recorded via sensing electrode poles 200, 203. Sensing signals can be recorded here between each of the sensing electrode poles 200, 203 and the housing 10 of the defibrillation generator 1 as counter-electrode. In addition, signals can be recorded between the sensing electrodes 200, 203, which together form a dipole. An ECG can be derived from the sensing signals, on the basis of which diagnostics and therapy management can be carried out for a possible defibrillation.

In the example shown in FIG. 2, each electrode lead 2A, 2B has a sensing electrode pole 203. Sensing signals can be recorded accordingly between the sensing electrode poles 203 of the electrode leads 2A, 2B (which together form a dipole). Additionally or alternatively, sensing signals can be recorded between the sensing electrode pole 203 of each electrode lead 2A, 2B and the housing 10 of the defibrillation generator 1 as counter-electrode. Again, an ECG can be derived from the sensing signals, which can be evaluated for diagnostics and therapy management.

In the example according to FIG. 3, the additional electrode lead 3 and the electrode array 30 arranged distally on it can be used, for example, for right-ventricular antibradycardic stimulation and/or antitachycardic stimulation (ATP=Antitachycardic Pacing). Additionally or alternatively, atrial and/or ventricular signals can be recorded via the electrode array 30 for the purpose of diagnostics and therapy management.

An electrode lead 3 can, for example, be added at a later time after an initial implantation of the defibrillation system, for example if slow ventricular tachycardias occur repeatedly in the patient or the sensing of signals for the purpose of diagnostics and therapy management is to be improved, because, for example, sensing via the non-transvenous electrode leads 2A, 2B is not sufficient.

Additionally or alternatively, a transvenous coronary sinus electrode can be connected to the defibrillation generator 1, for example, which can have an additional fourth connector for this purpose. Left ventricular stimulation and/or sensing can be performed via such a coronary sinus electrode.

Electrode leads 2, 2A, 2B, 3 can be marked by a suitable marking, for example a text, a colour marking or a radiopaque marking. Connectors 110, 112, 114 of the defibrillation generator 1 can also be marked.

Because an electrode lead assembly 4 consisting of the electrode leads 2, 2A, 2B is implanted non-transvenously, the defibrillation system is easy to implant. In particular, the defibrillation generator 1 can be implanted subcutaneously or submuscularly, for example below the collarbone of a patient. Electrode leads 2, 2A, 2B can, for example, be implanted parasternally using a tunnelling technique and may thus extend outside the patient's heart H.

The concepts forming the basis of the present invention are not limited to the embodiments described above, but can also be realized in other ways.

Electrode leads may be constructed differently from the examples presented and may in particular have different combinations and arrangements of electrode poles.

In this case, one or more electrode leads can be connected to a defibrillation generator, with at least some of the electrode leads being intended for non-transvenous implantation.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE SIGNS

1 Defibrillation generator
10 Housing
11 Connector block
110 Connector
111 Contact element
112 Connector
113 Contact element
114 Connector
115 Contact element
12 Control device
120 Control unit
121-123 Connector unit
124 Switching unit
125 Ventricular stimulation unit
126 Atrial stimulation unit
127 Cardioversion/defibrillation unit
13 Energy source (battery)
2, 2A, 2 Electrode lead
20 Electrode array
200, 201, 203 Sensing electrode pole
202 Defibrillation electrode pole
21 Plug
210 Connection terminal
3 Electrode lead
30 Electrode array
31 Plug
4 Electrode lead assembly
H Heart
RA Right atrium
RV Right ventricle

What is claimed is:

1. A defibrillation generator for an implantable defibrillation system, comprising:
   a housing;
   a connector block for connecting a non-transvenously implantable electrode lead assembly having at least one electrode lead and at least one defibrillation electrode pole; and
   a control device for controlling the operation of the defibrillation generator,
   wherein the connector block has two connectors, each connector of the two connectors is configured to connect to a single electrode lead of the electrode lead assembly,
   wherein the control device is configured to assume a first operating state when only one electrode lead is connected to one connector of the two connectors, the first operating state providing a first defibrillation function,
   wherein the control device is configured to assume a second operating state when two electrode leads, are connected to the two connectors, the second operating state providing a second defibrillation function,
   wherein each of the two electrode leads comprises a defibrillation electrode pole, an atrial sensing electrode pole for detecting atrial signals and arranged on a first side of the defibrillation electrode pole, and a ventricular sensing electrode pole for detecting ventricular signals and arranged on a second side of the defibrillation electrode pole,
   wherein the control device has a first receiving channel for processing ventricular signals received via the electrode lead assembly and a second receiving channel for processing atrial signals received via the electrode lead assembly, wherein the second receiving channel has a different gain and different filter characteristic than the first receiving channel for processing the atrial signals separately from the ventricular signals, and
   wherein each filter characteristic utilizes a cyclic time window to suppress interfering signals.

2. The defibrillation generator according to claim 1, wherein the connector block has a third connector for connecting an electrode lead to be transvenously implanted intracardially.

3. The defibrillation generator according to claim 2, wherein the connector block has a fourth connector for connecting a coronary sinus electrode lead to be transvenously implanted.

4. The defibrillation generator according to claim 1, wherein the housing of the defibrillation generator forms a counter-electrode to at least one defibrillation electrode pole of an electrode lead of the electrode lead assembly for delivering stimulation energy.

5. An implantable defibrillation system, comprising:
   an electrode lead assembly; and
   a defibrillation generator, comprising:
      a connector block for connecting a non-transvenously implantable electrode lead assembly having at least one electrode lead and at least one defibrillation electrode pole; and
      a control device for controlling the operation of the defibrillation generator,
      wherein the connector block has two connectors, each connector of the two connectors is configured to connect to a single electrode lead of the electrode lead assembly,
      wherein the control device is configured to assume a first operating state when only one electrode lead is connected to one connector of the two connectors, the first operating state providing a first defibrillation function, wherein the control device is configured to assume a second operating state when two electrode leads, are connected to the two connectors, the second operating state providing a second defibrillation function, wherein each of the two electrode leads comprises a defibrillation electrode pole, an atrial sensing electrode pole for detecting atrial signals and arranged on a first side of the defibrillation electrode pole, and a ventricular sensing electrode pole for detecting ventricular signals and arranged on a second side of the defibrillation electrode pole, wherein the control device has a first receiving channel for processing ventricular signals received via the electrode lead assembly and a second receiving channel for processing atrial signals received via the electrode lead assembly, wherein the second receiving channel has a different gain and different filter characteristic than the first receiving channel for processing the atrial signals separately from the ventricular signals, and wherein each filter characteristic utilizes a cyclic time window to suppress interfering signals.

6. The implantable defibrillation system according to claim 5, wherein at least one of the atrial sensing electrode pole and the ventricular electrode pole is designed as a ring electrode.

7. The implantable defibrillation system according to claim 5, wherein the at least one defibrillation electrode pole is designed as a helix.

8. The implantable defibrillation system according to claim 5, wherein the first electrode lead and/or the second electrode lead have at least one atrial sensing electrode pole for detecting atrial signals at a distal end of the electrode lead in question, remote from the defibrillation generator.

9. The implantable defibrillation system according to claim 5, wherein the first electrode lead and/or the second electrode lead have two atrial sensing electrode poles, forming a dipole, for detecting atrial signals.

10. The implantable defibrillation system according to claim 5, further comprising a third electrode lead for connection to a third connector of the connector block of the defibrillation generator, the third electrode lead being intended to be intravenously implanted in the heart.

11. The implantable defibrillation system according to claim 10, wherein the third electrode lead has an electrode array for intracardiac stimulation and/or sensing.

12. A method for configuring an implantable defibrillation system, comprising the steps of:

providing a defibrillation generator, which has a housing, a connector block for connecting to an electrode lead assembly, and a control device for controlling the operation of the defibrillation generator;

providing a non-transvenously electrode lead assembly comprising at least one electrode lead and at least one defibrillation electrode pole;

wherein the connector block has two connectors, each connector of the two connectors is configured to connect to a single electrode lead of the electrode lead assembly;

configuring a switching unit of the control device to assume a first operating state when only one electrode lead is connected to one connector of the two connectors, the first operating state providing a first defibrillation function;

configuring the switching unit of the control device to assume a second operating state when two electrode leads, are connected to the two connectors, the second operating state providing a second defibrillation function, wherein each of the two electrode leads comprises a defibrillation electrode pole, an atrial sensing electrode pole for detecting atrial signals and arranged on a first side of the defibrillation electrode pole, and a ventricular sensing electrode pole for detecting ventricular signals and arranged on a second side of the defibrillation electrode pole, wherein the control device has a first receiving channel for processing ventricular signals received via the electrode lead assembly and a second receiving channel for processing atrial signals received via the electrode lead assembly, wherein the second receiving channel has a different gain and different filter characteristic than the first receiving channel for processing the atrial signals separately from the ventricular signals, and wherein each filter characteristic utilizes a cyclic time window to suppress interfering signals.

* * * * *